US005503145A

United States Patent [19]

Clough

[11] Patent Number: 5,503,145

[45] **Date of Patent: *Apr. 2, 1996**

[54] COMPUTER-CONTROLLING LIFE SUPPORT SYSTEM AND METHOD FOR MIXED-GAS DIVING

[76] Inventor: Stuart Clough, 11 Hillside Close, Ellington, Huntingdon, Cambs. PE18 OAR, England

[ * ] Notice: The portion of the term of this patent shall not extend beyond the expiration date of Pat. No. 4,939,647.

[21] Appl. No.: 274,906

[22] Filed: Jul. 14, 1994

Related U.S. Application Data

[63] Continuation of Ser. No. 901,507, Jun. 19, 1992, abandoned.

[51] Int. Cl.[6] .......................... B63C 11/02; A61M 16/00; A62B 7/00; F16K 31/02

[52] U.S. Cl. ................................ 128/204.22; 128/201.27; 128/202.22; 128/205.11; 128/205.23

[58] Field of Search ......................... 128/201.27, 201.28, 128/204.18, 204.21, 204.22, 204.23, 204.26, 205.23, 202.22, 205.11

[56] References Cited

U.S. PATENT DOCUMENTS

| | | | |
|---|---|---|---|
| 3,695,261 | 10/1972 | Emmons | 128/204.23 |
| 4,056,098 | 11/1977 | Michel et al. | 128/204.23 |
| 4,192,001 | 3/1980 | Villa | 128/205.23 |
| 4,285,339 | 8/1981 | McIntyre | 128/204.23 |
| 4,658,358 | 4/1987 | Leach et al. | 128/204.23 |
| 4,876,903 | 10/1989 | Budinger | 73/865.1 |
| 4,882,678 | 11/1989 | Hollis et al. | 128/204.23 |
| 4,939,647 | 7/1990 | Clough et al. | 128/201.27 |
| 4,949,072 | 8/1990 | Comerford et al. | 128/204.23 |
| 4,964,404 | 10/1990 | Stone | 128/204.22 |

*Primary Examiner*—Kimberly L. Asher
*Attorney, Agent, or Firm*—Raymond L. Greene

[57] ABSTRACT

A computer-controlled life support system and method for mixed-gas diving, having separate supplies of oxygen and diluent gas or gases is provided. Multiple processor units provide redundant gas control and dive data recording. The primary processor automatically controls the oxygen make-up based on partial pressure of oxygen according previously determined dive parameter. A secondary CPU provides back up gas control information and displays system and dive parameters including decompression schedules. A tertiary CPU, independently powered and provided with duplicate sensors, provides an additional backup means for gas control and decompression calculations. No automatic gas control is available from the third CPU, but displayed data allows manual gas control.

11 Claims, 12 Drawing Sheets

COMPUTER-CONTROLLING LIFE SUPPORT SYSTEM AND METHOD FOR MIXED-GAS DIVING

This is a continuation, of application Ser. No. 07/901,507 filed Jun. 19, 1992 now abandoned.

FIELD OF THE INVENTION

The present invention relates to diving systems and more specifically to self-contained, mixed-gas breathing devices.

BACKGROUND OF THE INVENTION

Self-contained diving systems are well-known in the art and systems are well-developed which permit diving to depths of approximately 500 meters. Self-contained systems fall into two general categories, air diving in which compressed air is used as breathing gas and secondly, mixed gas diving in which the diver is supplied with one or more artificial mixtures of gases, suitable for the depth and phase of the operation.

Traditionally, this split between air and mixed gas diving has taken place at depths of 50 meters (165 feet). For diving operations to less than 50 meters compressed air would normally be used, while for depths of greater than 50 meters mixtures of helium and oxygen would typically be used.

While air is a satisfactory breathing gas on or near the surface, it has serious limitations as a diving gas. As a diver proceeds below 50 meters, the increasing ambient pressure progressively renders air unbreathable. This condition results from two causes: nitrogen, which constitutes approximately 79% of air, becomes narcotic as ambient pressure increases; and oxygen, which constitutes approximately 21% of air, becomes toxic under the same conditions. To overcome these effects, the diver is fed artificial breathing mixes consisting of helium and oxygen, helium/nitrogen and oxygen, hydrogen/helium oxygen, neon and oxygen or exotic mixtures of deuterium and oxygen. When mixed in the correct proportions such breathing mixtures enable diving operations to be carried out at considerable depth. The maximum depth of such operations has not yet been determined. However, one limiting factor for a self-contained system is the large volume of breathing gas required. As the diver descends, gas consumption increases rapidly and is determined by the following expression; gas usage at a given depth per minute equals gas usage at surface for the given work load, multiplied by the absolute pressure. Additionally, even a short duration dive at depth requires an extended de-compression time. For example, a dive to 160 meters for only 15 minutes requires approximately seven hours of decompression. Although a diver in this example may ascend rapidly to approximately 40 meters, he must spend approximately six more hours ascending from 40 meters to the surface. Typically, these long decompression times allow a brief duration dive using a self-contained system to approximately 200 meters as a practical limit due to the volume of breathing mix which must be carried even with closed circuit equipment.

From the foregoing discussion, it can be seen that the diver's breathing mixture must meet certain criteria. The diluent gas should be relatively inert and have no appreciable narcotic or other detrimental effect. The breathing mixture must have adequate oxygen content to support life but not so great content as to produce toxicity and must be supplied at a suitable pressure and temperature. The critical factor in controlling the oxygen content is the partial pressure of constituent oxygen ($ppO_2$).

Partial pressure of oxygen in a particular mixture is the pressure oxygen alone would have if the other gases were removed from a fixed volume of mixture. The physiological effect of oxygen depends upon its partial pressure in a mix, becoming increasingly toxic as the partial pressure increases above the normal level found in air at sea level. Typically at sea level, the partial pressure of the oxygen constituent of air being 0.21 bar.

There are two major expressions of oxygen poisoning, one which affects the central nervous system (CNS) and the other which affects the lungs. CNS poisoning becomes a significant factor as the partial pressure of oxygen approaches 2.0 bar. It gives rise to various symptoms, the most serious of which is a convulsive seizure, similar to an epileptic fit. These seizures last for about two minutes, and are followed by a period of unconsciousness. The diver will regain consciousness after some 15 minutes to repeat the symptoms if the oxygen pressure remains unchanged. The obvious danger to a diver is the loss of control while in the diving environment and the resultant danger of drowning. The point at which an individual diver will be affected by CNS oxygen poisoning varies widely and is also significantly affected by workload. As such, various companies and navies have laid down guidelines for the maximum permissible oxygen partial pressures under various circumstances. Typically, values between 0.8 bar and 1.8 bar are used for diving operations and 0.3 bar to 0.5 bar for storage while in saturation. Storage while in saturation refers to operation wherein divers are recovered from depth in a closed and pressurized diving bell and then transferred under pressure to a chamber complex, typically onboard ship. Saturation refers to a technique employed for deep commercial diving operations. As discussed previously, as time at depth increases so the time necessary to decompress increases. However, a state is reached after which further increases in bottom time do not further increase the time to decompress. This state is referred to as saturation. Typically divers are stored at pressure in the chamber complex for several days or weeks, transferred to a bell for work periods and then lowered to the sea floor. At the end of the period, the system is then slowly decompressed over a period of several days or weeks, depending on the depth at which the system was operating.

Pulmonary oxygen poisoning, on the other hand, results from prolonged exposure to oxygen partial pressures above 0.5 bar, and causes irritation and damage to the lungs. The onset of this form of poisoning is insidious and progressive, and is not as dramatic as CNS oxygen poisoning. It will be apparent from the foregoing that the $ppO_2$ in a breathing mix should be kept to less than 1.8 bar and above 0.2 bar. This range is quite wide and there are, optimum values appropriate to different circumstances as discussed further hereafter.

Phases of decompression can create a preferential diffusion gradient for the elimination of the inert gas load. Typically for the deep dive, the descent and bottom time would be completed on helium/oxygen mixes. During the course of the decompression, an inert gas change to neon or possibly nitrogen would be made, which would have the effect of speeding-up the elimination of the helium absorbed at depth while limiting the absorption of the second applied inert gas.

Additionally, current closed circuit systems off-gas both oxygen and diluent gas. This off-gassing typically occurs on descent where the pre-set pressure of oxygen is greater than the pressure in the initial stages of the dive. For example, a pre-set pressure of 1.8 bar may be used during descent to limit the up-take of inert gas. With this setting, oxygen off-gassing occurs from the surface down to approximately 8 meters. Likewise during ascent, off-gassing also causes excessive use of the breathing mix gases.

The net effect of these limitations is that open circuit compressed air diving is limited to approximately 50 meters in depth and similarly open circuit mixed gas diving is limited to approximately 100 meters in depth. Also closed circuit mixed gas diving is also currently limited to approximately 100 meters due to the problems of off-gassing and less than optimal oxygen set point. Compressed air diving is limited because the oxygen partial pressure is too low during the initial descent, thereby causing a greater absorption of nitrogen. Thereafter, the partial pressure of oxygen is too high causing oxygen poisoning and, because of the high absorption of nitrogen, the possibility of nitrogen narcosis. Finally, the partial pressure of oxygen is too low on ascent causing an extended decompression time. Likewise, the lack of control of oxygen partial pressure in self contained mixed gas diving limits the practical depth. First, the off-gassing of oxygen during the initial part of the dive reduces the available oxygen and then the lack of partial pressure control extends the decompression time on ascent. Finally, off-gassing again occurs during the final ascent. The problems of off-gassing and sub-optimal oxygen partial pressure control limit the effective depth of self contained diving systems to approximately 100 meters by the inability to carry sufficient breathing mix to meet the required time for decompression.

SUMMARY OF THE INVENTION

It is an object of the invention to provide a system for diving having oxygen saving features to avoid off-gassing.

It is another object of the invention to provide a means of automatically and continuously adjusting the partial pressure of oxygen within the diver's breathing mix.

It is yet another object of the invention to provide a mixed diluent gas.

A further object of the invention is to provide a means of reducing the oxygen partial pressure as depth decreases during the latter phases of decompression.

It is an object of the present invention to provide a self-contained diving system suitable for dives to depths of approximately 200 meters. Used in association with a deep diving system or submersible the equipment may be used to significantly greater depths.

Accordingly, the invention is a self-contained computer-controlled, personal life support system for mixed gas diving. The system includes storage and supply systems for oxygen and for one or more diluent gases. A means for chemically removing carbon dioxide is also provided. The system is controlled by a plurality of central processor units operated by custom firmware which allow the oxygen partial pressure ($ppO_2$) to be maintained at an optimum level appropriate to the depth and phase of the dive. The system monitors depth and time and provides for automatic changes of $ppO_2$ consistent with the progress of the dive. A means of manual override is available for use in the event of failure of the automatic gas control system.

The unit also provides a means of accurately recording all parameters of the dive, for use by surface monitors or supervisors and for subsequent dive analysis. Provision is also made for several spare data collection channels to be available for use as required by the end user.

BRIEF DESCRIPTION OF THE DRAWINGS

These and other features, objects, and advantages of the present invention will be better appreciated from an understanding of the operative principles of a preferred embodiment as described hereinafter and as illustrated in the accompanying drawings wherein.

Figure 5:
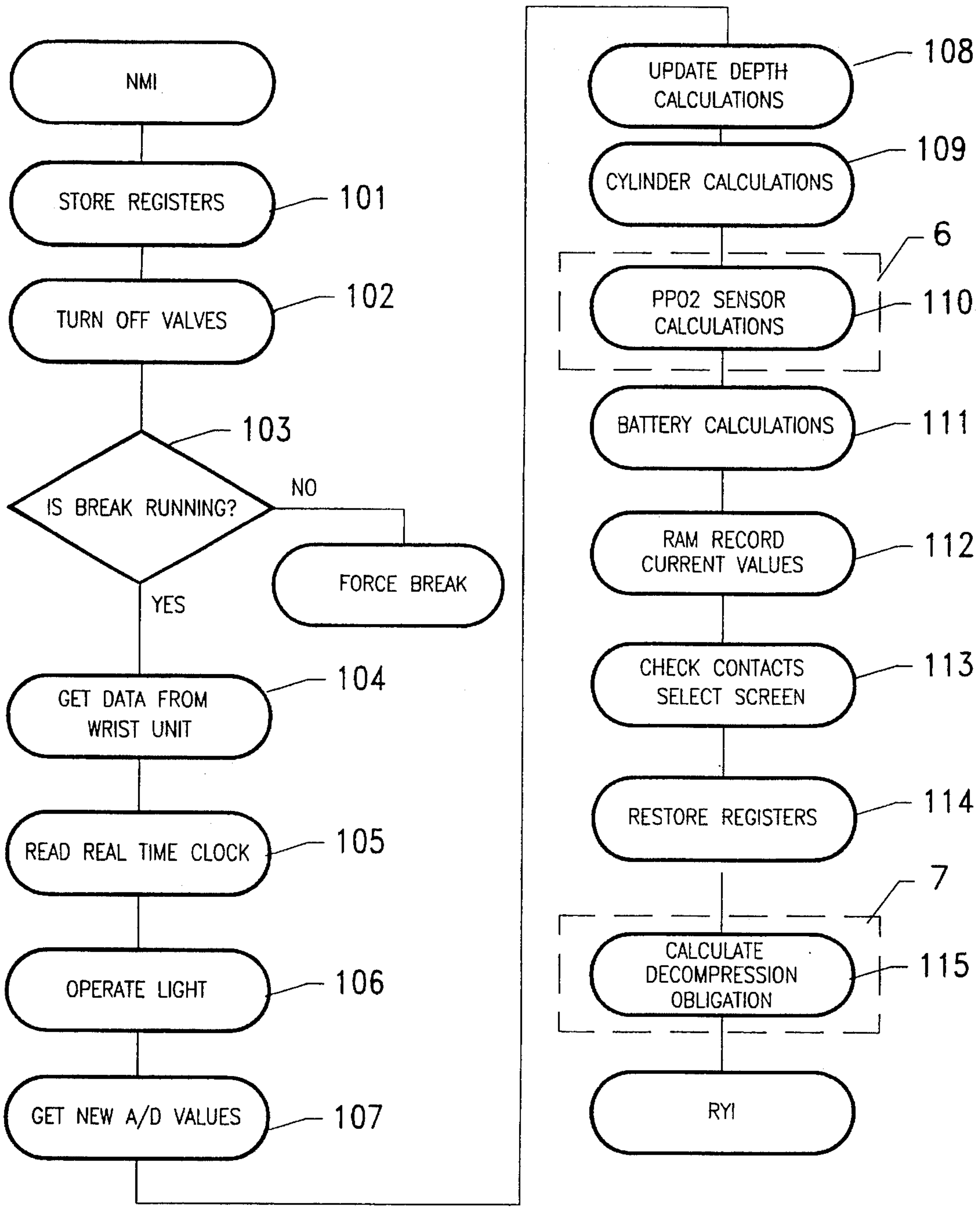
Figure 6A:
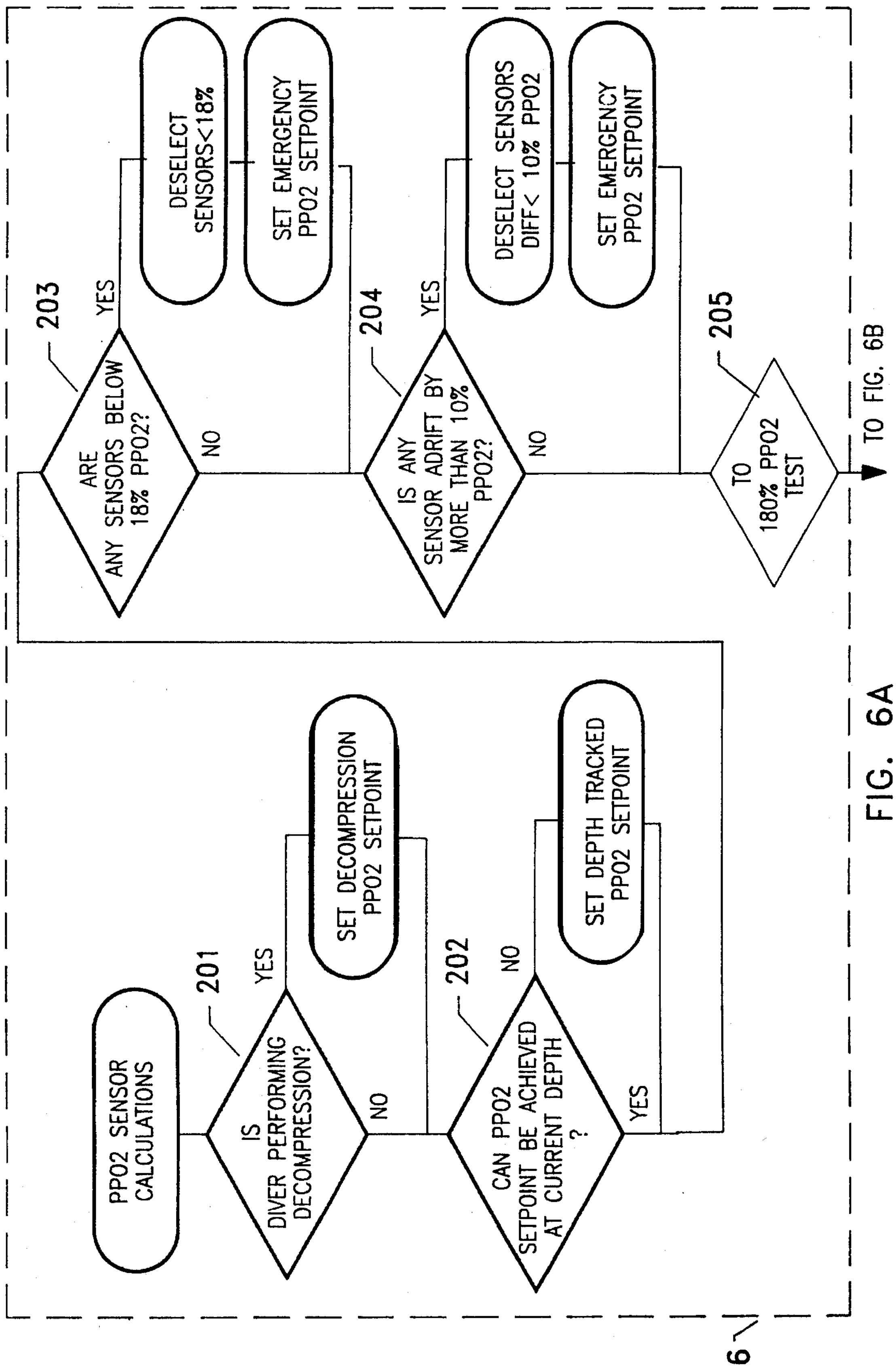
Figure 6B:
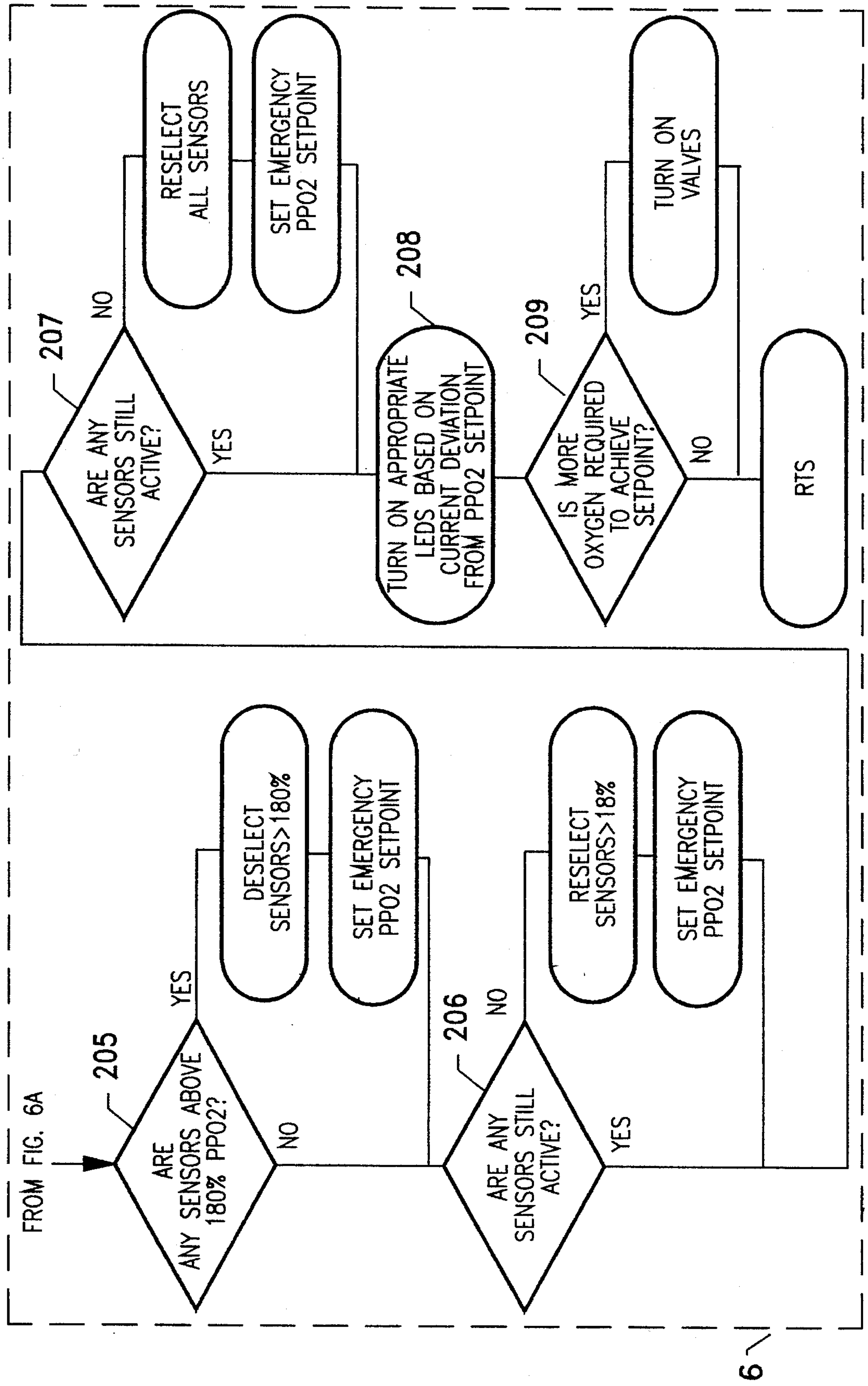

FIG. **3*a*** is a schematic of the system primary electronic control unit contained within the back-pack;

FIG. **3*b*** is a schematic of the system secondary electronic control unit associated with wrist display processing and dive monitoring;

FIG. **3*c*** is a schematic of the independently powered gas and dive monitoring system;

FIGS. **4*a* and 4*b*** are functional flow diagrams for the power up sequence of the unit and initiation of gas control;

FIG. 5 is a functional flow diagram for gas control sequence, dive monitoring and decompression calculations;

FIGS. **6*a* and 6*b*** are functional flow diagrams for $ppO_2$ control and $ppO_2$ warning systems, respectively.

Figure 7:
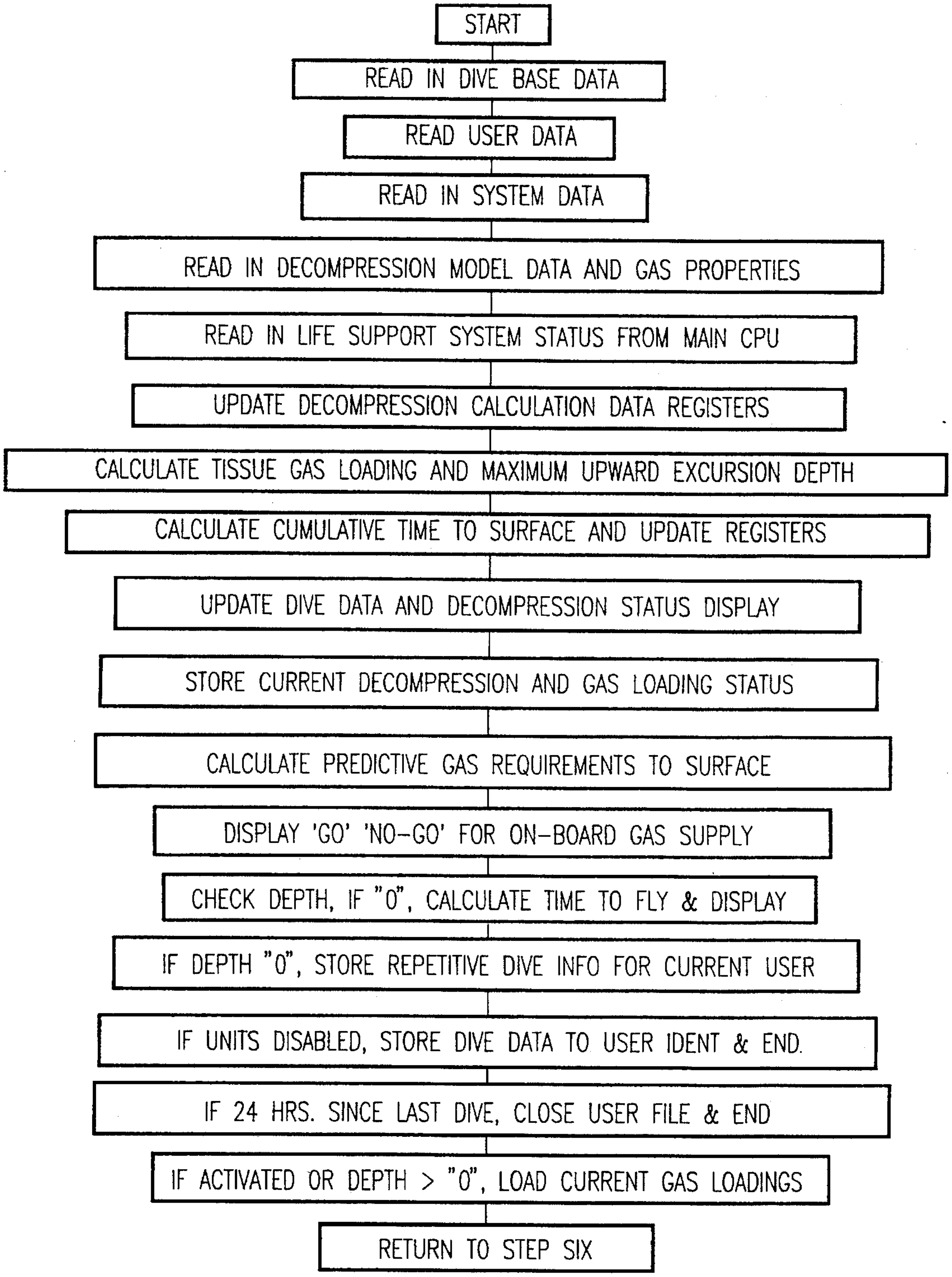

FIG. 7 is a chart showing decompression calculations; and

Figure 8:
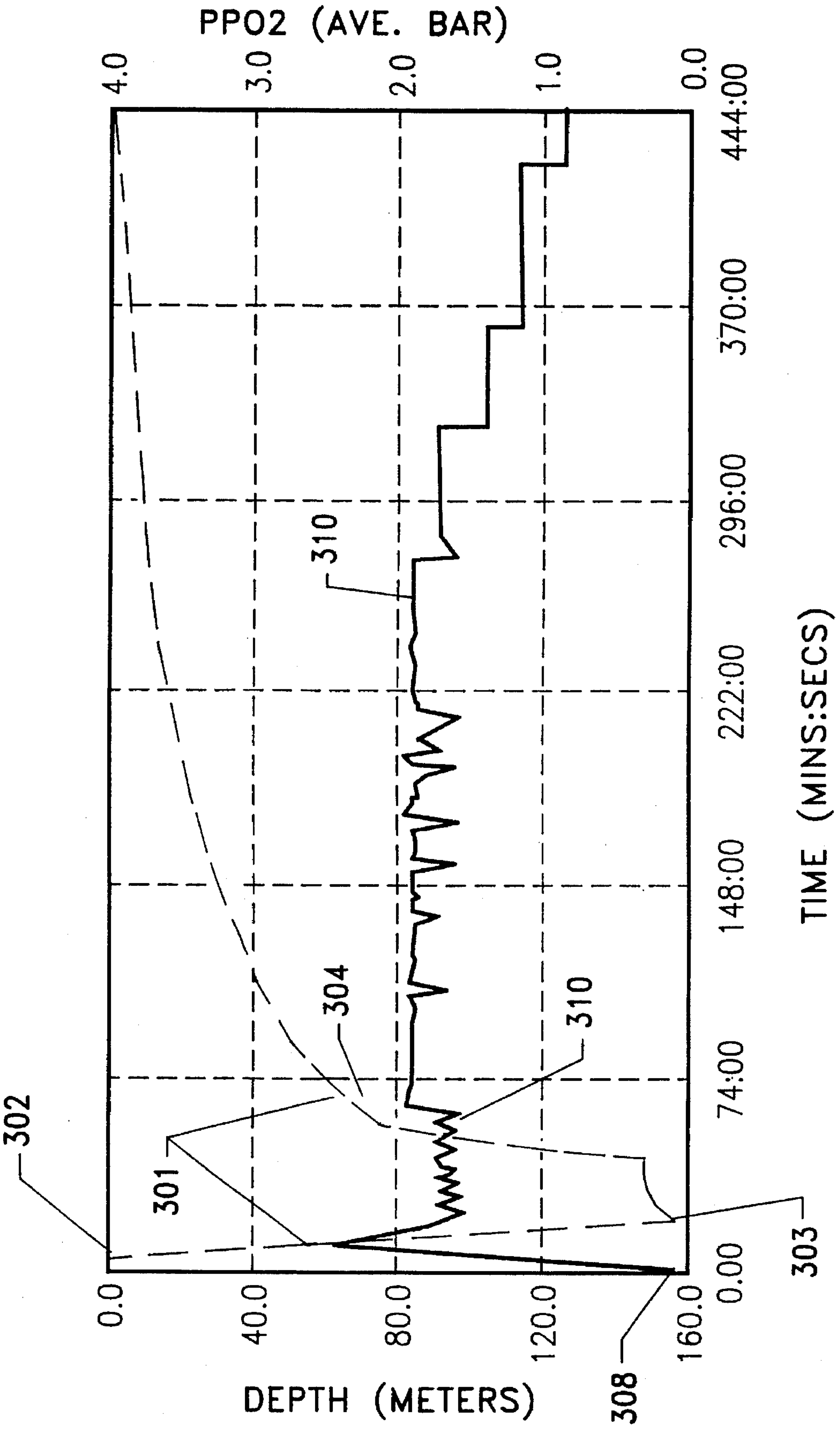

FIG. 8 is a chart showing a typical dive profile.

DETAILED DESCRIPTION OF THE INVENTION

Figure 1:
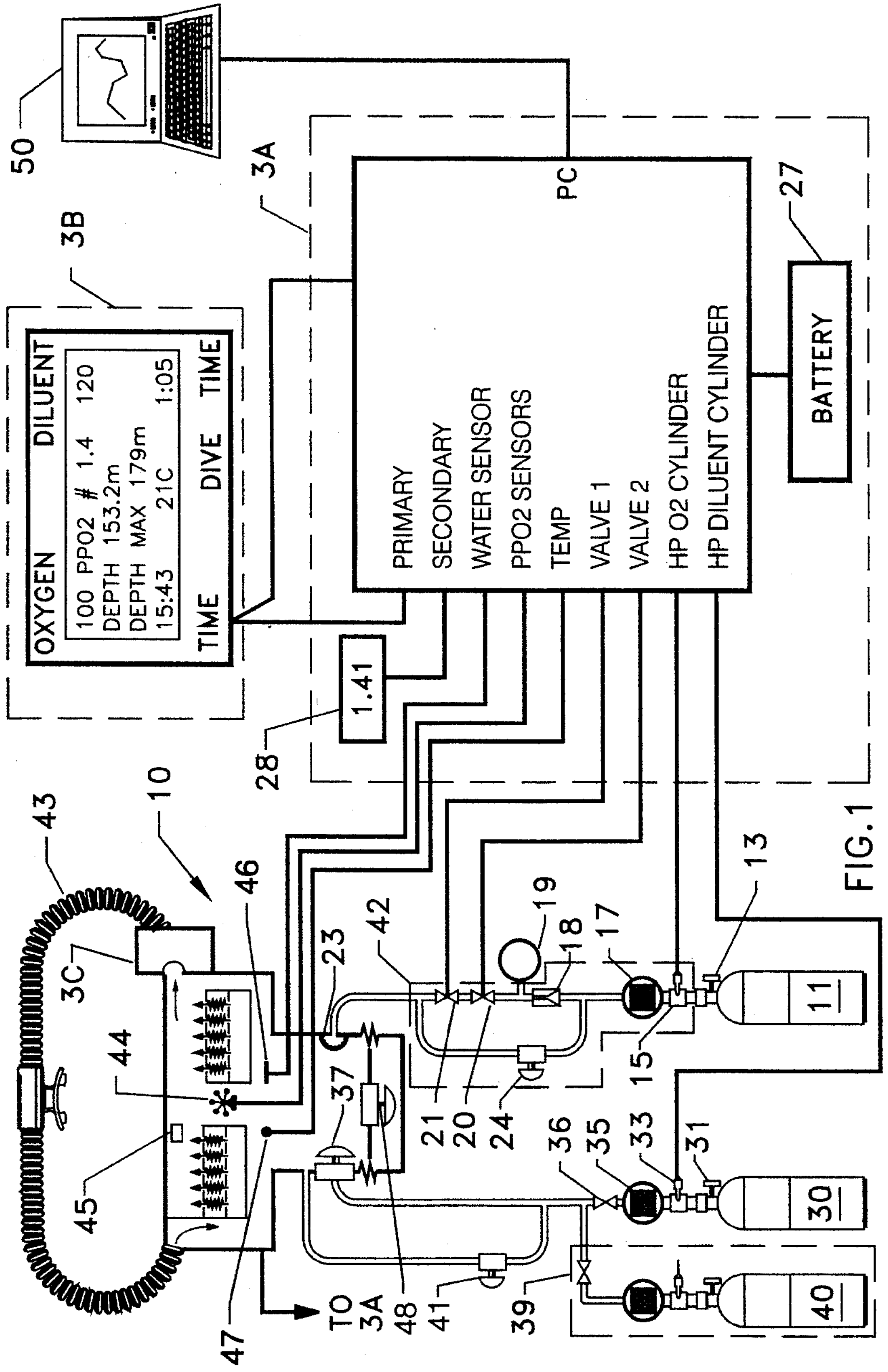
FIG. 1 is a general mechanical layout of the mixed-gas life support equipment with main components shown.

Referring now to FIG. 1, the overall mechanical arrangement of the personal life support system, denoted generally by the reference numeral 10, is shown with its major components identified. The personal life support system 10 comprises an oxygen storage bottle 11, with isolating valve 13, electronic pressure transducer assembly and pressure reducing regulator 15, which is linked to the primary CPU **3*a* and filter assembly 17. The filter assembly 17, is connected to an orifice plate 18, an accumulator 19, and electrically actuated valves 20 & 21, which are linked to the primary and secondary CPU's 3*a* and 3*b*, respectively, and to the main oxygen inlet diffuser 23. The valves 20 and 21 may be by-passed in the event of failure of the automatic control by the manual oxygen addition valve 24. While two electrically operated valves are shown in FIG. 1**, the unit will operate satisfactorily with only one valve. The inclusion of a second electrically actuated valve is optional and dependent on the particular applications for which the equipment is intended and upon user preference.

Similarly, diluent gas is supplied from storage bottle 30 via isolating valve 31, pressure transducer and regulator assembly 33, filter 35 to hydrostatic diluent gas addition valve 37, to the breathing loop 43. Optionally, an alternate diluent gas may be supplied from bottle 40 by alternate inert gas system 39. Crossflow between the inert gas storage cylinder is prevented by non-return valve 36. Dotted box 42 includes various individual components to regulate filter and control bypass gas flow into the breathing bag. These components may be integrated into a single unit.

The hydrostatic inert gas inlet valve 37 may in the event of failure be by-passed through manual activation of valve 41, which admits inert gas to the breathing loop.

The automatic control of the system is provided by the primary CPU 3*a* and secondary CPU 3*b*. Back-up manual control is supported by the additional gas and dive monitoring module 3*c*.

The breathing loop 43, comprising conventional breathing hoses, mouth piece, full face mask or helmet, breathing bag and chemical carbon dioxide absorbent or molecular sieve, are not novel to this invention. Within the breathing loop are contained a plurality of oxygen sensors 44, and optionally a carbon dioxide sensor 45 and water sensors (not shown). These sensors are linked to the primary and secondary CPU's 3*a* & 3*b* and to the back-up gas and dive monitoring module. Provision is made for the inclusion of additional temperature sensors (not shown) which interface with the primary CPU, to record breathing loop gas temperature, in addition to ambient water, chamber, submersible or bell temperature.

Electrical power for the equipment is provided from battery pack 27. The secondary display 28 provides a backup means of monitoring the breathing loop $ppO_2$ in the event of primary CPU failure.

The primary and secondary CPU's may optionally be linked by umbilical or through-water communications system to a surface monitoring unit 50. The surface unit 50 comprises a module configured for surface monitoring, for example, a conventional personal computer operating with custom software.

Figure 2:
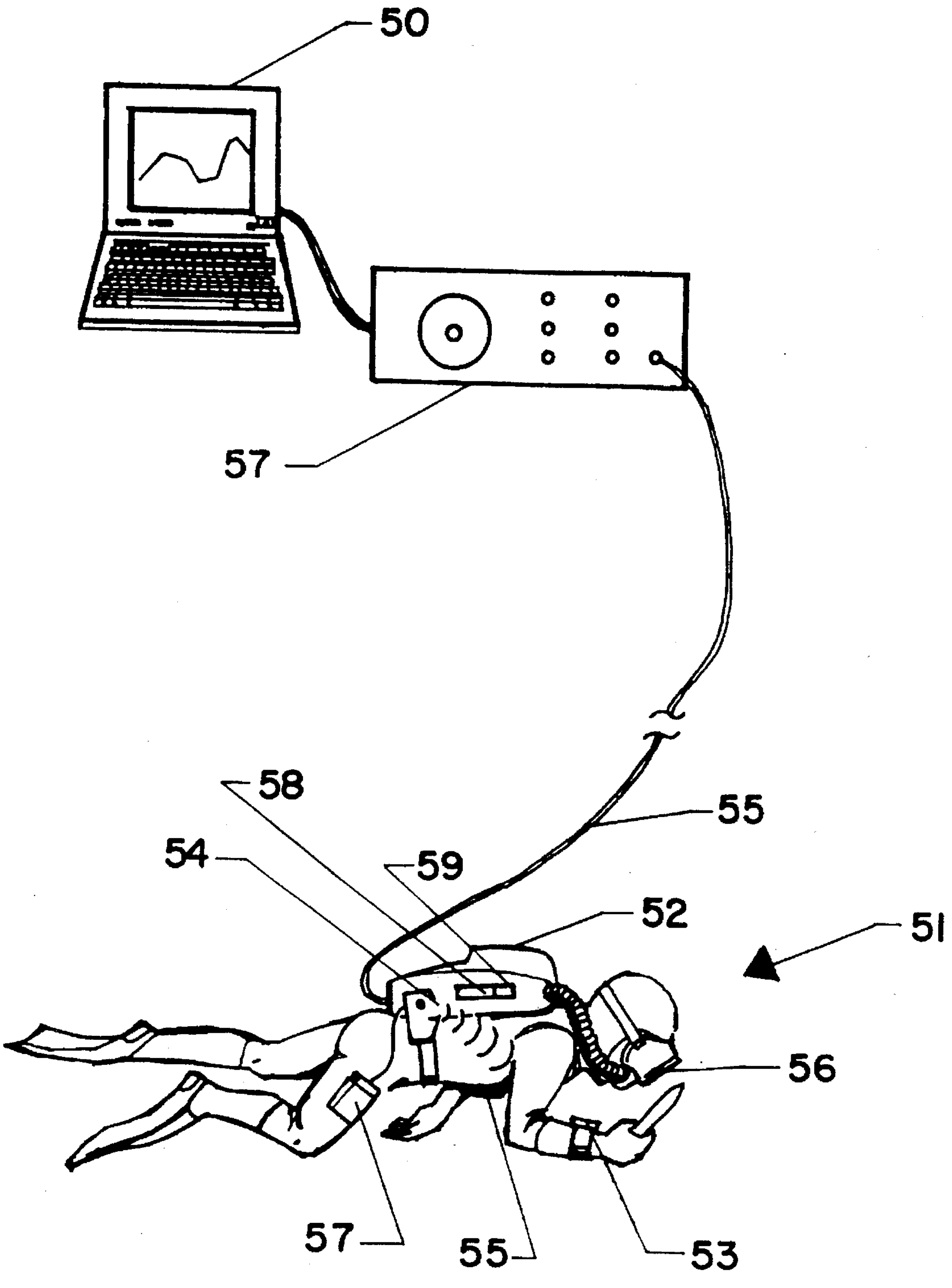
FIG. 2 shows the unit as carried by the diver when in use.

FIG. 2 shows the system as it would be worn for autonomous operation by the diver 51. The backpack 52 contains the major mechanical and electrical components of the system including gas supplies, chemical carbon dioxide removal means and electronic control system. The status of the equipment and current dive information are displayed to the diver by wrist unit 53 or console 55. The data from the main CPU is transmitted to the display console 55, by cable or, through water transmission system and transducer 54. The unit may be linked to the surface by umbilical 85 to provide communication and dive data up-link. This link to the surface may be by hard wire, acoustic through water transmission, electromagnetic or a variety of similar means. The display console 55 may optionally be replaced by the Head-Up Display, (HUD) module 56 which provides the diver with a continuous display of the system and dive data within the normal field of view. The HUD may be fitted within a full face mask or a helmet. The surface computer system 50 may also be connected to a communication system 87.

Figure 3A:
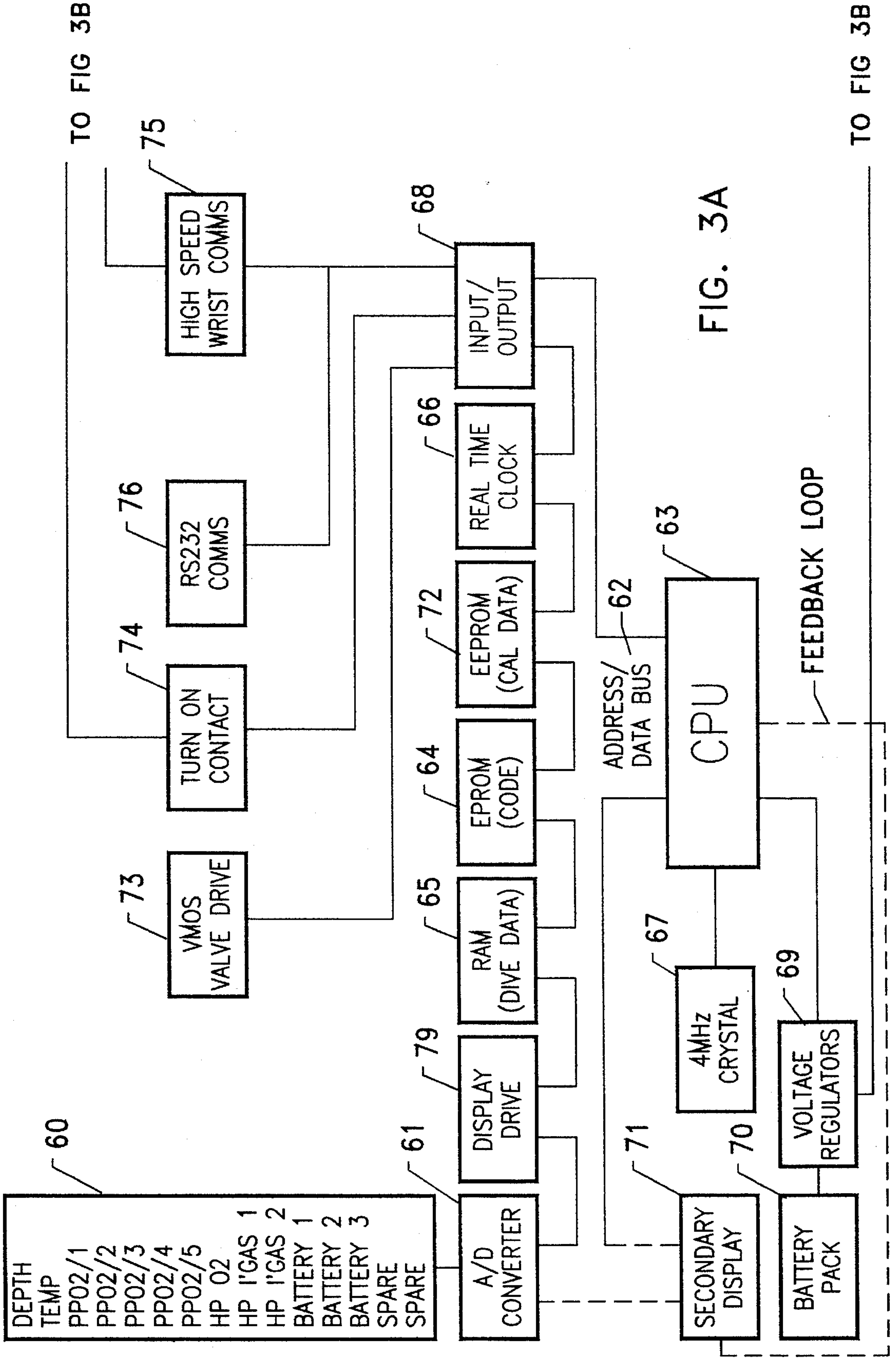
Figure 3B:
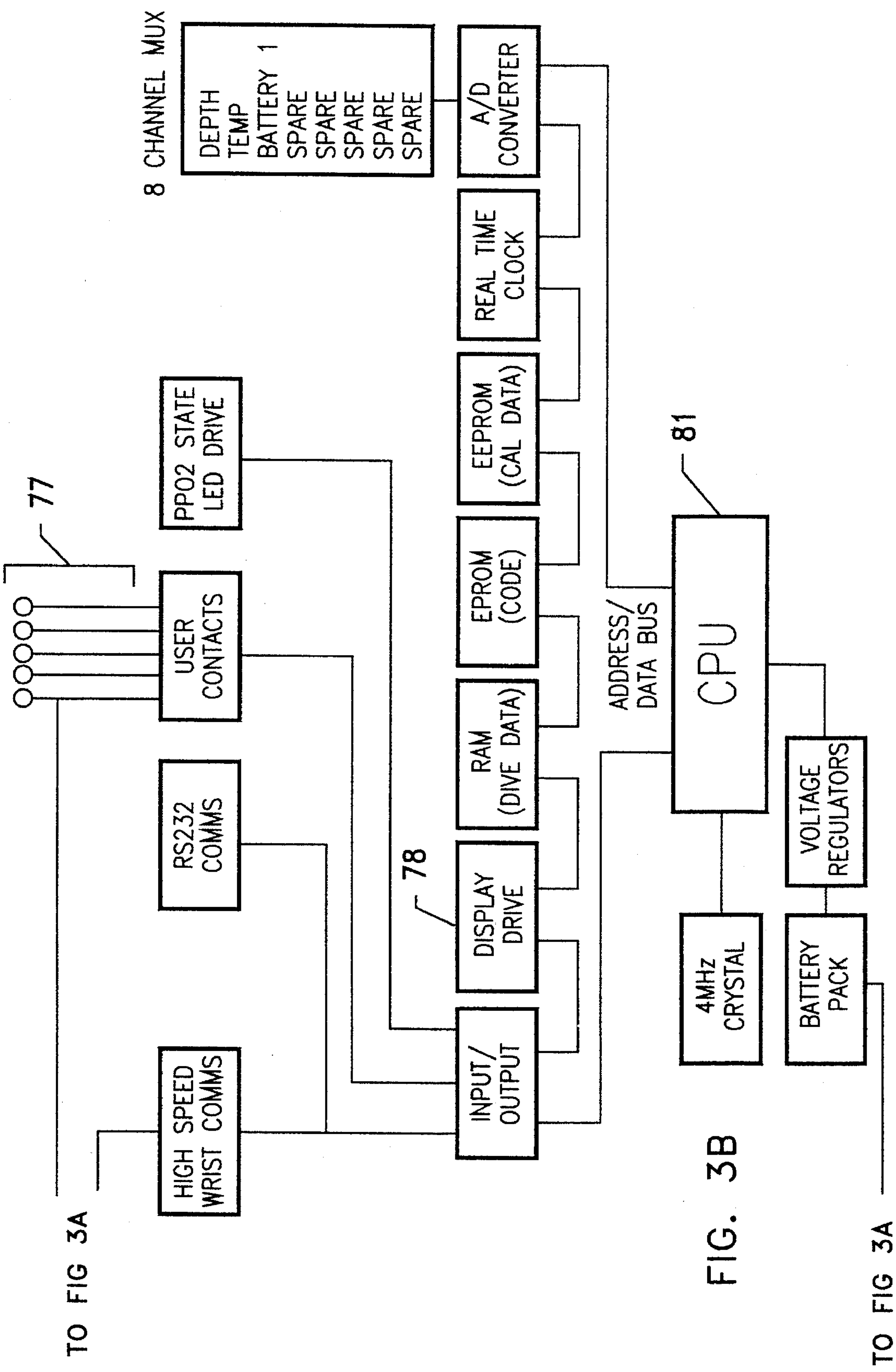

FIGS. 3*a* and 3*b* are to be viewed side-by-side as noted to show the interconnections.

Referring to FIG. 3*a*, the primary CPU comprises an interface to a plurality of system sensors 60 linked to analog-to-digital converter (A/D converter) 61. The A/D converter 61 is linked to the primary CPU 63 via address/data bus 62. The primary CPU 63 derives its operating instructions from custom EPROM 64 and writes dive data to RAM 65.

Essential peripheral components are clock 66, crystal 67, input/output controller 68, and power supply and voltage regulators 69 & 70. A secondary display 71 supported by the CPU 63 is provided and set up in such a way that once calibrated the functioning of the CPU is not required for breathing loop $ppO_2$ to be measured and indicated on the secondary display. A feed back loop is however provided to enable the CPU to monitor the secondary system for data integrity while the CPU is functioning and verify the calibration procedure. This configuration provides for additional safety and redundancy in the unlikely event of CPU failure, be that mechanical or electrical. The sensor off-sets and calibration data for all sensor elements linked to the primary CPU are held in EEPROM 72 which is protected by a conventional memory protection battery (not shown in this diagram). The input/output controller 68 interfaces with the VMOS drivers 73 and conventional power control circuitry to the electric oxygen addition valves 20 and 21 of FIG. 1. The turn on contacts 74 are linked to the secondary CPU and display processor shown in more detail as FIG. 3*b*. The communications between the primary and secondary CPU are controlled by high speed wrist/console communications 75. The primary CPU and stored dive data can be accessed by an external computer or surface display via the RS232 communications protocol interface 76. Display driver 79, is not normally used unless additional audio or visual warning and display modules are connected. The primary means of displaying system status to the user is via display and display drivers of module shown in FIG. 3*b*.

FIG. 3*b* shows in more detail the secondary CPU 81 and remote display processing unit. The unit comprises the same major components as in 3*a*, with the addition of the user contacts 77. These contacts are used to control menu selections from the system wrist display 78 and to turn the unit on. This module may optionally be disconnected from the primary CPU contained within the backpack for continued use as a dive data recording unit if the diver undertakes a surface decompression procedure.

Surface decompression refers to the technique in which the diver exits the water before completing the required decompression. Thereafter, the diver transfers to a deck chamber and is then recompressed to an appropriate depth, after which a modified decompression is completed in the surface chamber system.

The backpack may be used with any number of different modules 3*b*, to support use by multiple users and surface decompression procedures. Each user may optionally have a personal module 3*b*, configured with custom firmware and personal details that may then be used with any backpack.

Figure 3C:
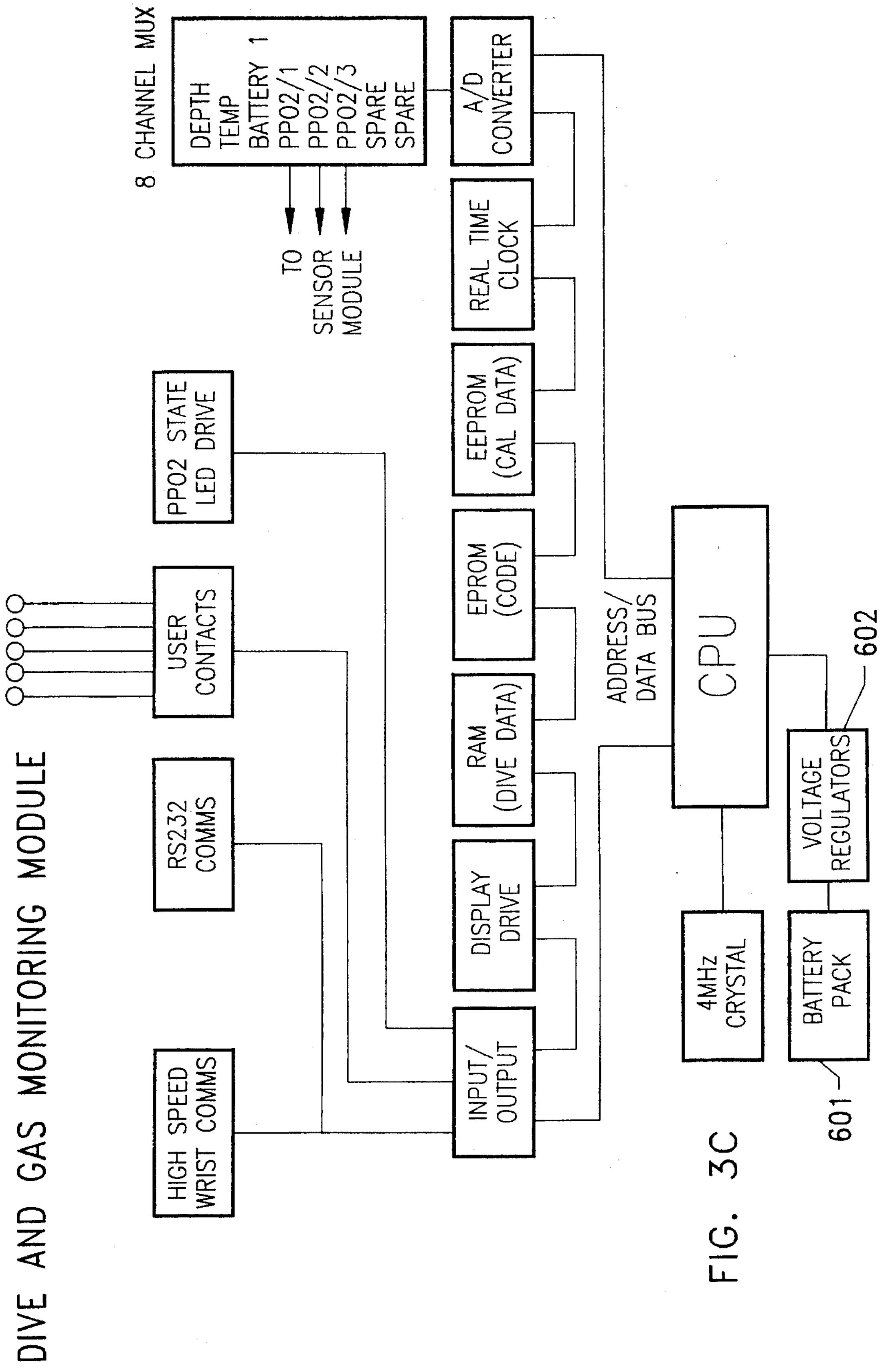

Referring now to FIG. 3*c*, a block schematic for the independently powered gas and dive monitoring system. This module provides for totally independent monitor of gas, dive time, depth, and decompression obligation in the event of the failure of the primary and secondary CPU's and the failure of the secondary display. It is essentially the same as module 3*b* with the addition of an independent power supply and regulation 601 and 602. The module has program and memory space as in FIG. 3*b* and may be separately calibrated before the dive. The module would usually be secured to the backpack 52 of FIG. 2 until actually needed for use by the diver. The use of this module is not essential to the functioning of the equipment and would typically be applicable only to advanced or extreme diving conditions.

Figure 4A:
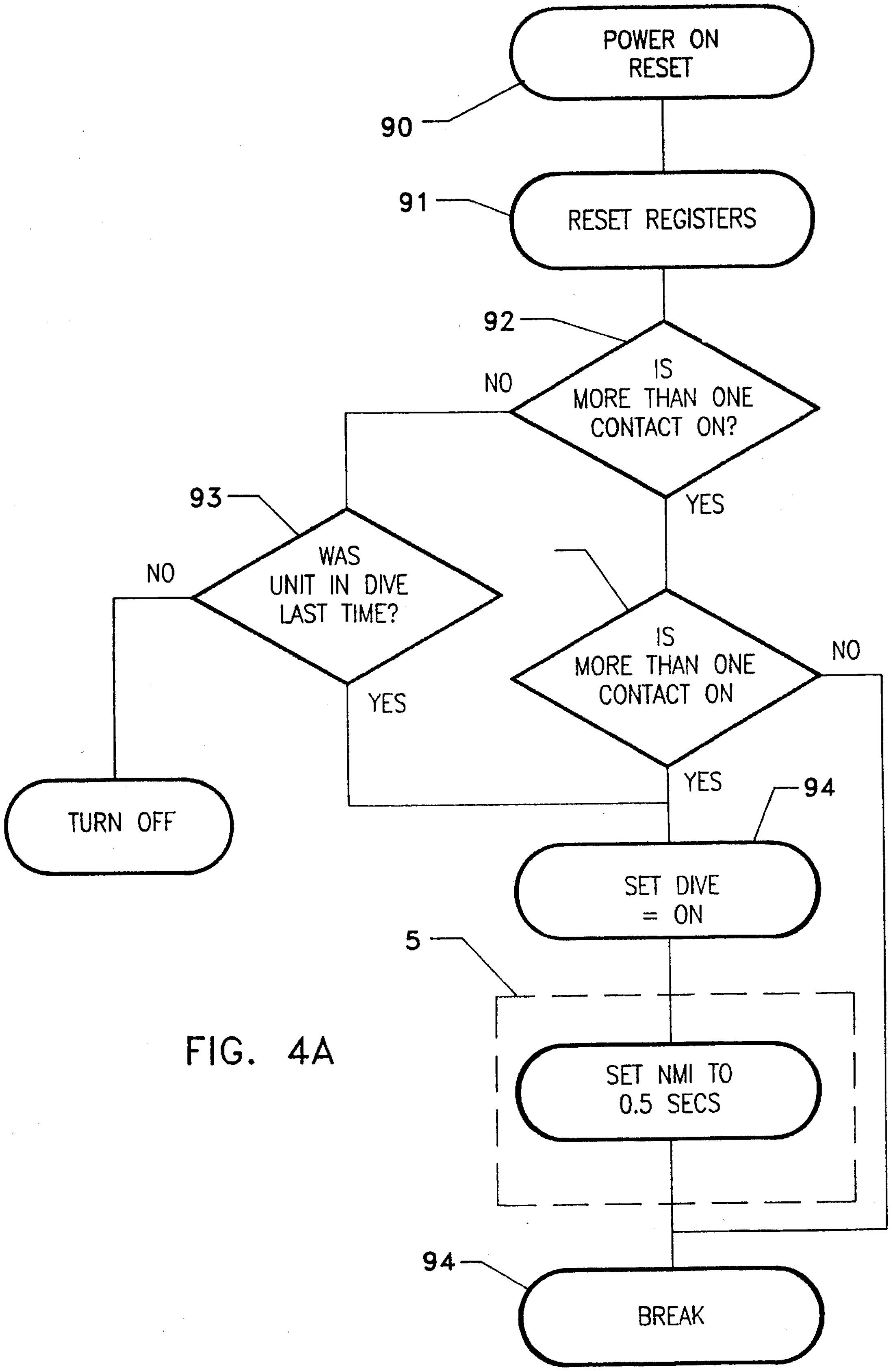

FIGS. 4A, 5, 6A, 6B, describe the operation of the custom firmware. Referring now to FIG. 4*a*, a functional flow chart of the power-up and initiation of gas control by the life support system is shown. The sequence of steps follows. At Power-On 90, CPU registers are Reset Registers 91 and a decision logic is activated to check for More Than One Contact On 92 and if not, whether the dive is continuing underway, Was Unit in Dive Last Time 93. If yes, the process continues through Set Dive On and setting of NMI(Numerical method integration). (Set NMI shown in the dotted box 5). Set NMI is shown in detail in FIG. 5 hereinafter.

Figure 4B:
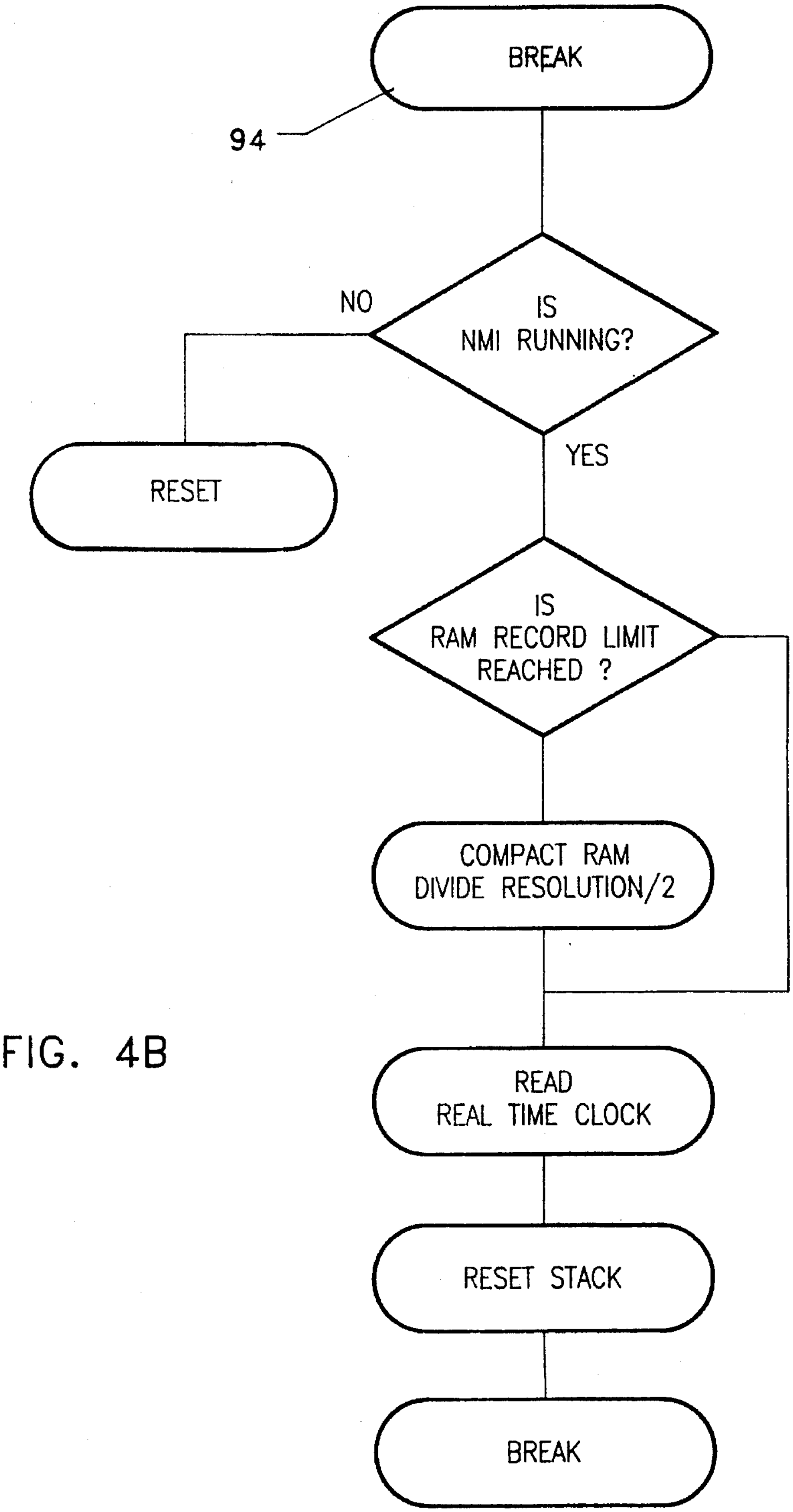

Referring now to FIG. 4*b*, the flow chart of events after break 94 continue with routines to compact the dive data recording if extremely long dives are undertaken or if the dive data has not been down loaded to a surface computer. It is a necessary constraint that any data storage device has some finite capacity. This is also the case with the dive data storage devices used in the preferred embodiment of the invention. In order to ensure that dive data is not completely lost when the memory device limit is reached, the resolution is divided by two, or effectively the data collection sample interval is doubled and memory space provided by over-writing every other record. The routines described check the available data storage space, if the limit is reached the resolution is divided by two and the memory compacted. The routines loop to monitor memory usage.

Referring now to FIG. 5, a functional flow diagram for the process for gas control, dive monitoring and decompression is shown. The gas control process initiates with the storing sensor data and set-point parameters 101 the setting all valves to OFF or Closed 102. The BREAK route 103 to check memory space and compact dive data recording as previously described. Reading of data and operating parameters 104 stored at the wrist or display console are correlated with the real time clock 105. From pre-set operating criteria, or depth data the wrist console light is actuated 106 and all sensors are read at 107. The raw sensor data for depth is corrected and processed at 108 followed by correction and processing of gas supply pressures 109. The raw data from the oxygen sensors is then processed 110 and oxygen addition valves, warnings and alarms activated accordingly. Battery condition calculations 111 are completed and all sensor and read out data is stored in RAM 112. Display output is provided by Check Contacts/Select Screen 113. Thereafter registers are restored 114, and the decompression obligation is calculated 115 before beginning another cycle of the program. Dotted box 7 represents the process of determining the decompression obligatio, a subroutine shown in FIG. 7. The details of oxygen control subroutine 6 are shown in more detail in FIGS. **6*a* and 6*b*** (to be viewed together as noted).

Referring to FIG. **6*a* and 6*b*, the control of oxygen partial pressure proceeds as follows. The selection of current oxygen set-point is determined from initiation parameters in the main program previously referred to and by decision logic 201. The dive run phase or decompression phase set point having been determined, a check 202 is made against current depth to determine if the target set point can actually be achieved. If the current depth is less than the target set point, then depth tracking is engaged and the sequence continues to validate each sensor in turn. The individual sensor response check 203 is completed and any sensor showing an error condition is deselected. In the event that this check 203 finds one or more sensors in error, the emergency phase oxygen set point is selected and warnings activated. If no errors are detected at this stage, the sequence continues to sensor deviation check 204. If sensor deviations are detected at this stage, the emergency oxygen set-point is be selected and warnings are activated. If the sensors are within the allowed tolerance, the program continues with a high level oxygen check at step 205. Step 206 checks the remaining active sensors or reselects all sensors and emergency set-point. If sensors are active and within tolerance, then the display console 'light emitting diodes' and data screen are updated at step 208 and additional oxygen is admitted if required at step 209**. The program then returns to the start and repeats until the system is deactivated.

Referring now to FIG. 7, the functional steps in computing the decompression profile are shown. To effectively manage a dive the system must be able to take into account the users recent dive history, the planned excursion in order to access gas requirements and be able to deal with any deviations, planned or accidental from the proposed dive plan. The program is initiated by manual switch at or by the dive system sensing pressure on the depth transducer or water on the sensing contacts of the display console. When activated, the equipment dive data is be loaded by the Read in Dive data Base step. If activated by water or depth only, the unit assumes a set of default dive initiation settings and warns, the user of these settings. The user may exit the water and initialize the system with the correct personal data or continue in the knowledge that default settings are in use. The base data relating to the dive includes target oxygen set points, and ppO2 change criteria. Read User Data reads in from memory, computer interface or command console the individual user data and previous dive history. In order to make allowance for previous recent dives the user has the option to read-in a personal data file or confirm that no previous dives are to be taken into account during the calculation of decompression obligation for the forthcoming dive. Read in System Data reads in equipment and system data, battery life gas capacity followed by loading of the decompression model.

The decompression model is that algorithm or formula used to mathematically model the gas uptake of the body during the course of a dive or series of dives and then to model the gas elimination during decompression. Several of these models or algorithms are in general use and specific PROGRAMS may be written for each of the various methods. The use may then optionally select the preferred model for the proposed dive.

Update Decompression Model allows the program to read the current dive system status including depth rate of change of depth, oxygen partial pressure within the breathing loop and time. The values so obtained are used by the current program to calculate, record and display the current decompression obligation.

Typically this would be shown as a maximum upward excursion from the present depth. For example, while the maximum upward depth remains set to 0, the diver is within the no-decompression range and may ascend directly to the surface at the prescribed rate. As a decompression obligation is accumulated the depth shown would increase, As the decompression obligation increases it is important for the diver to know not only the depth of the next stop that must be made, but also to know the total time it will take to regain the surface. Calculate Cumulative Time, Update Dive Data, and Store Current Decompression steps complete the calculations and display the current stop depth and remaining decompression time to the surface.

Predictive gas use calculations provide a check on gas remaining vs. gas required to complete the drive.

The remaining steps monitor the continuing position and as 0 depth is reached, display further time remaining before a flight may be made, reactivating the system if a repetitive dive is made or write the data to memory and deactivate the program. The effect of the various steps refereed previously hereto are more clearly shown by the chart of a typical dive as shown in FIG. 8.

FIG. 8 depicts a typical dive profile to nearly 160 meters represented by profile line 301. As depicted, the dive begins at the surface 302 with the diver descending rapidly to maximum depth 303, the scale along the left ordinate providing a depth scale and the scale along the horizontal axis providing a time in minutes. Dive profile 301 shows that the diver remains near the maximum depth 303 for approximately fifteen minutes. Thereafter, he ascends fairly rapidly to approximately one-half his maximum dive depth, depth 304. From that point on, the diver must spend nearly six more hours decompressing. The chart further shows the $ppO_2$ line 310 over time as measured against the right hand ordinate showing pressure in bars. As can be noted at the beginning of the diving, the initial $ppO_2$ 308 is low to prevent off-gassing, however, $ppO_2$ is maintained as high as possible without inducing oxygen poisoning so that inert gas uptake will be maintained as low as possible. During the main workload of the dive at the maximum depth 303, $ppO_2$ is reduced to an $O_2$ work level. Once ascent begins, the $ppO_2$ is again increased to reduce decompression time by increasing removal of diluent gases. Finally, as the surface is approached, a reduced $O_2$ level is set to present off-gassing and save oxygen.

The advantages and novel features of the new diving system are numerous and allow a greatly enlarged diving envelope, that is greater depth and duration. First, a calibration facility is provided to allow automatic or manual entry of atmospheric pressure prior to the dive. Calibration at pressure is also provided for use with an available decompression chamber. Oxygen control is greatly improved providing additional safety and reducing off-gassing. Second, a depth tracking is provided on descent to avoid gas wastage on the surface prior to the dive. If for example, a run phase $ppO_2$ of 1.4 bar is selected, the unit will control to 0.9 bar on the surface 1.0 bar at 1 meter water depth, 1.1 bar at 2 meters water depth and at 5 msw would engage normal set point control of 1.4 bar. This facility will function for any desired set point. Third, changes in $ppO_2$ may be selected to engage during the course of a dive. For example, a higher $ppO_2$ may be selected part way through the ascent to further optimize decompression. Typically, the system is set to automatically increase the $ppO_2$ set point as the diver ascends to 50% of the maximum depth of the dive. Fourth, as the decompression proceeds and the diver gets nearer to the surface, a point is reached at which depth and $ppO_2$ set point are equal, i.e., the diver is on 100% oxygen. For example, if the decompression phase set point is selected to be 1.8 bar, 100% oxygen mix is reached at 8 meters water depth. As the decompression continues and the diver ascends further the $ppO_2$ is automatically reduced to avoid off gassing and waste of on-board oxygen supplies. Fifth, provision is also made for two diluent gases. For extreme depth, these gases are helium and neon or helium and nitrogen. Changing diluent gas at the appropriate point further optimizes decompression. Additionally, the system provides a completely self-contained decompression computer with a complete independent back up system.

Although the invention has been described relative to a specific embodiment thereof, there are numerous variations and modifications which will be readily apparent to those skilled in the art in light of the above teachings. It is therefore to be understood that, within the scope of the appended claims, the invention may be practiced other than as specifically described.

What is claimed as new and desired to be secured by Letters Patents of the United States is:

1. A computer-controlled life support system for mixed gas diving comprising:

a breathing loop;

means for supplying oxygen to said breathing loop;

means for supplying diluent gas to said breathing loop;

a main central processor unit receiving data from the sensor group consisting of partial pressure of oxygen, depth, time, storage tank pressure, battery level data, inspired gas temperature, carbon dioxide absorbent temperature, carbon dioxide gas levels, and breathing loop flood alarm data functionally connected to said means for supplying oxygen and providing oxygen flow so as to achieve a continuously variable partial pressure of oxygen in said breathing loop as determined by dive parameters including depth, dive profile, and time;

a detachable secondary central processor unit receiving data from the sensor group consisting of partial pressure of oxygen, depth, time, storage tank pressure, battery level data, inspired gas temperature, carbon dioxide absorbent temperature, carbon dioxide gas levels, and breathing loop flood alarm data functionally connected via data link to the primary CPU functionally connected to said means for supplying oxygen and providing oxygen flow so as to achieve a continuously variable partial pressure of oxygen in said breathing loop as determined by dive parameters including depth, dive profile, and time; and a tertiary central processor unit linked directly by a data cable to duplicate sensors including data from the sensor group consisting of partial pressure of oxygen, depth, time, storage tank pressure, battery level data, inspired gas temperature, carbon dioxide absorbent temperature, carbon dioxide gas levels, and breathing loop flood alarm data, thereby providing redundant back-up for the life support system.

2. A computer-controlled life support system as in claim 1 wherein the tertiary central processor unit includes an independent power supply.

3. A computer-controlled life support system as in claim 1 wherein said the tertiary central processor unit further comprises an independent dive data display.

4. A computer-controlled life support system as in claim 1 wherein said breathing loop is a semi-closed circuit rebreather.

5. A computer-controlled life support system as in claim 4 wherein said semi-closed circuit rebreather has a continuous flow of mixed gas.

6. A computer-controlled life support system as in claim 1 wherein said breathing loop is a closed circuit rebreather.

7. A computer-controlled life support system as in claim 4 wherein said closed circuit rebreather further comprises an oxygen injection system having continuously variable output.

8. A computer-controlled life support system as in claim 1 wherein the data link is by wire cable.

9. A computer-controlled life support system as in claim 1 wherein the data link is by optical fiber.

10. A computer-controlled life support system as in claim 1 wherein the data link is by wireless acoustic transmitter and receiver.

11. A computer-controlled life support system as in claim 1 wherein the data link is by wireless electrical-field transmitter and receiver.

* * * * *